Figure 1:
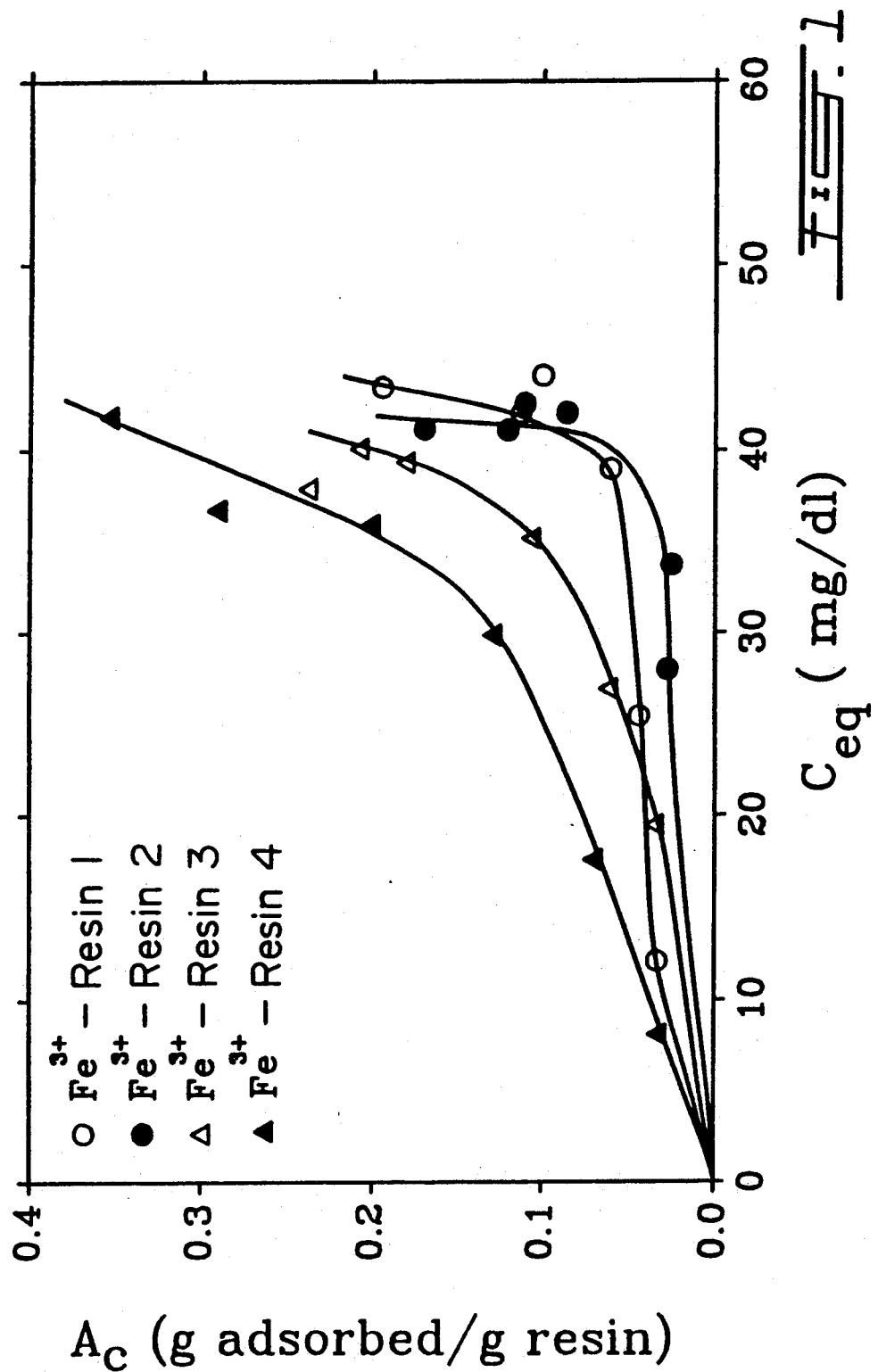

United States Patent [19]

St. Pierre et al.

[11] Patent Number: 5,114,709
[45] Date of Patent: May 19, 1992

[54] FERRIC ION COORDINATED POLYAMINE RESINS FOR THE LOWERING OF BLOOD CHOLESTEROL

[75] Inventors: Leon E. St. Pierre, Frelighsburg; George R. Brown, Dollard-des-Ormeaux; Gaoming Wu, Montreal; Youlu Yu, Verdun, all of Canada

[73] Assignee: Lowchol Scientific Inc., Frelighsburg, Canada

[21] Appl. No.: 713,875

[22] Filed: Jun. 12, 1991

[51] Int. Cl.$^5$ ............................................. A61K 31/74
[52] U.S. Cl. ................................. 424/78.12; 514/892; 514/911; 525/371
[58] Field of Search .................... 424/78, 79; 514/892, 514/911

[56] References Cited

U.S. PATENT DOCUMENTS

| | | | |
|---|---|---|---|
| 3,692,895 | 9/1972 | Nelson | 424/79 |
| 4,759,923 | 7/1988 | Buntin | 424/439 |
| 4,902,501 | 2/1990 | Bandi | 424/79 |

Primary Examiner—Thurman K. Page
Assistant Examiner—Raj Bawa
Attorney, Agent, or Firm—Swabey Ogilvy Renault

[57] ABSTRACT

The invention is concerned with a metal ion coordinated polyamine resin in which a non-toxic, pharmaceutically acceptable chelating metal ion is coordinated with a cross-linked and non-digestible polymeric amine selected from the group consisting of: (a) polyamine resins with a hydrophilic backbone, of the formula:

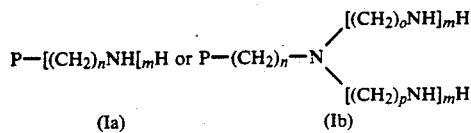

(Ia)        (Ib)

wherein P represents a hydrophilic, cross-linked and non-digestible homopolymer backbone, m is an integer varying from 1 to 10 inclusive, and n, o and p are, independently, integers varying from 2 to 12 inclusive; (b) polyamine resins with a hydrophobic backbone, of the formula:

$$P'-[NH(CH_2)_n]_m NH_2 \qquad (II)$$

wherein P' represents a hydrophobic, cross-linked and non-digestible homopolymer backbone, m is an integer varying from 0 to 6 inclusive and n is an integer varying from 2 to 12 inclusive; and (c) cross-linked copolymers of a polyethylenepolyamine containing from 2 to 6 ethylene units and epichlorohydrin. The metal ion coordinated polyamine resins of the invention are highly efficient sorbents for bile acids and salts and can thus be used for reducing hypercholesterolemia in affected humans.

27 Claims, 5 Drawing Sheets

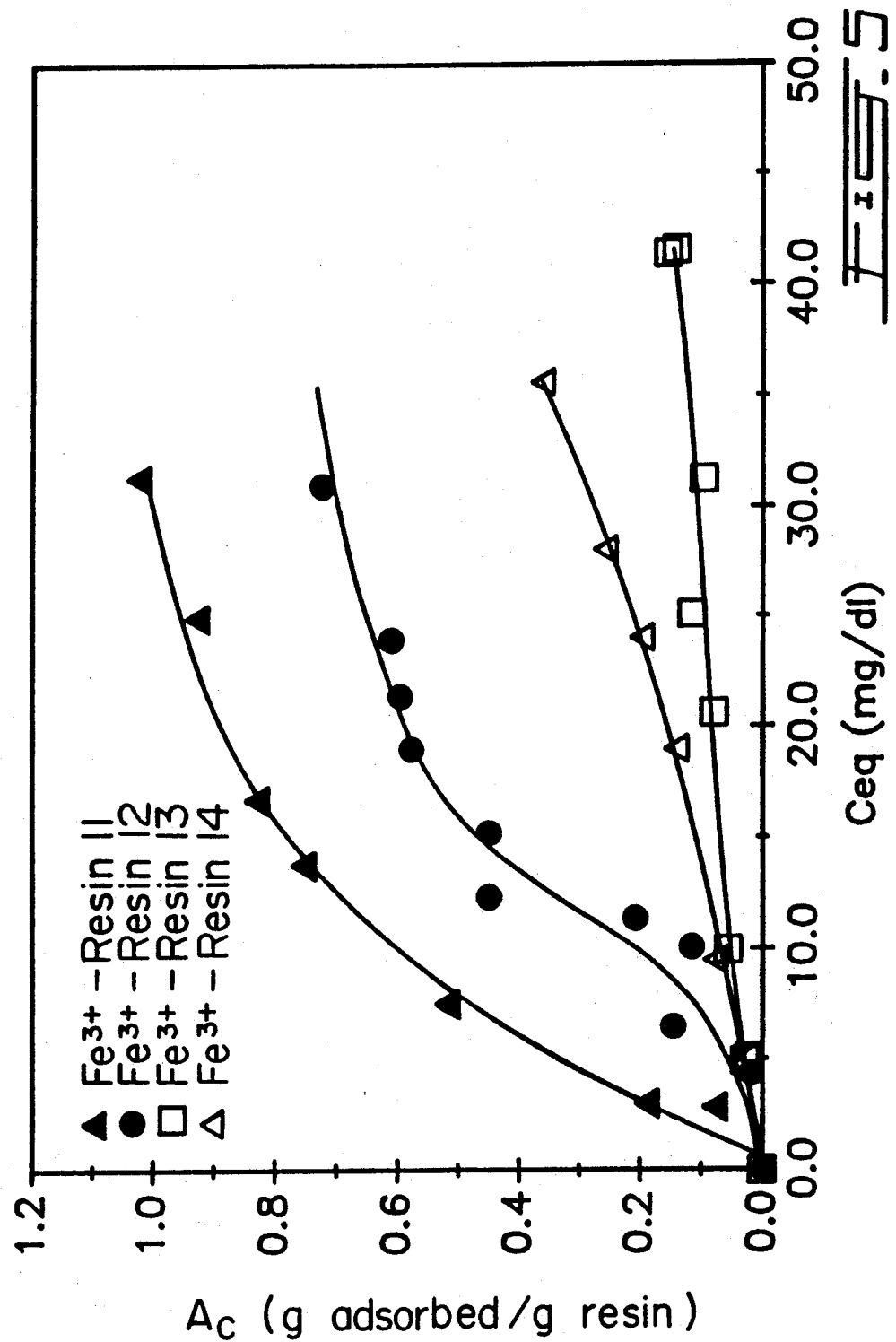

FERRIC ION COORDINATED POLYAMINE RESINS FOR THE LOWERING OF BLOOD CHOLESTEROL

The present invention relates to novel ingestible metal ion coordinated polyamine resins which are useful as sorbents for bile salts. More particularly, the invention is directed toward the treatment of hypercholesterolemia by removing through sorption the bile acids and salts from the small intestine, thereby increasing the catabolism of cholesterol in the liver with a concomitant decrease in the blood cholesterol level.

All available evidence indicates that the incidence of higher than normal blood serum cholesterol levels in humans is associated with atheroslerosis and other hypercholesterolemic disease signs. Hypercholesterolemia, the leading cause of death in many countries, is presently treated by restricted and special dietary intake, inhibition of cholesterol synthesis, accelerated catabolism and prevention of gastrointestinal adsorption, i.e., interruption of enterohepatic circulation. Increased catabolism of cholesterol can be achieved by the oral administration of bile salt binding agents.

Cholestyramine, the most widely used adsorbent for bile salts, is a copolymer of polystyrene and divinylbenzene with quaternary ammonium groups as functional groups. Being a typical strongly basic ion exchanger, its counterions of the quaternary ammonium, usually chloride ions, are exchanged with bile salt anions during the binding. The hydrophobic nature of the polymer backbone results in its poor biocompatibility. As a consequence, adverse side effects have been experienced by hypercholesterolemic patients. The drug has to be taken in large dosage and may cause stomach discomfort to patients.

Metallic salts (e.g. $FeCl_3$) and oxides (e.g. $Al(OH)_3$) which can form insoluble precipitates with bile salts have also been employed. However, these agents consisting of small species are absorbable, causing acute and chromic toxicity hazards and preventing their further application.

Although widely used, non-absorbable sorbents such as the positively charged amine containing materials sold under the trade marks QUESTRAN and COLESTID have the setbacks of low adsorption capacity and undesirable side effects and are not completely satisfactory. Since hypercholesterolemia is a well recognized cause of cardiovascular disease, new and better drugs are urgently needed to replace the existing materials.

It is therefore an object of the present invention to overcome the above drawbacks and to provide novel bile salt sorbents with high sorption capacities, specificity and biocompatibility.

In accordance with the invention, there is provided a novel metal ion coordinated polyamine resin in which a non-toxic, pharmaceutically acceptable chelating metal ion is coordinated with a cross-linked and non-digestible polymeric amine selected from the group consisting of:

a) polyamine resins with a hydrophilic backbone, of the formula:

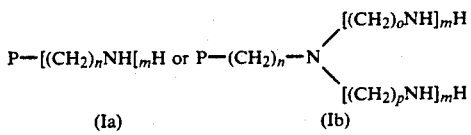

wherein P represents a hydrophilic, cross-linked and non-digestible homopolymer backbone, m is an integer varying from 1 to 10 inclusive, and n, o and p are, independently, integers varying from 2 to 12 inclusive;

b) polyamine resins with a hydrophobic backbone of the formula:

wherein P' represents a hydrophobic, cross-linked and non-digestible homopolymer backbone, m is an integer varying from 0 to 6 inclusive and n is an integer varying from 2 to 12 inclusive; and c) cross-linked copolymers of a polyethylenepolyamine containing from 2 to 6 ethylene units and epichlorohydrin.

It has been found quite unexpectedly that by attaching metal ions which react with bile salts through electrostatic interaction, onto non-absorbable, cross-linked polymers through coordination, and by selecting polymers differing in hydrophobicity and the number of amine functionalities, the sorption capacity and specificity of the final product can be optimized. The metal ion coordinated polyamine resins according to the invention are therefore highly efficient sorbents for cholic acid and glycocholic acid as well as other bile acids, such as chenodeoxycholic acid, lithocholic acid, deoxycholic acid and taurocholic acid.

The significance of bile acid sorption is related to the lowering of serum cholesterol. As it is known, cholesterol is a major and probably the sole precursor of bile acids during normal digestion, bile acids are secreted via the bile from the liver and the gallbladder into the intestine. Bile acids emulsify the fat and lipid materials present in the foods, thus facilitating adsorption. A major portion of bile acids secreted is reabsorbed from the intestines and returned via the portal circulation of the liver, thus completing the enterohepatic cycle. The binding of bile acids in the intestines onto an insoluble sorbent that is excreted in the feces results in partial removal of bile acids from the enterohepatic circulation, preventing their readsorption. The increased fecal loss of bile acids leads to an increased oxidation of cholesterol to bile acids, a decrease in beta lipoprotein or low density lipoprotein serum levels, and a decrease in serum cholesterol level. Thus, the compounds of the invention can be used for reducing hypercholesterolemia in affected humans.

Accordingly, the present invention also provides, in a further aspect thereof, a method of treating hypercholesterolemia in an affected human, which comprises administering to the affected human an effective amount of a bile salt sorbent consisting of a metal ion coordinated polyamine resin as defined above.

According to yet another aspect of the invention, there is provided a pharmaceutical composition for the treatment of hypercholesterolemia, which comprises as active ingredient a metal ion coordinated polyamine resin as defined above, together with a pharmaceutically acceptable carrier therefor.

A preferred non-toxic, pharmaceutically acceptable chelating metal ion is a ferric ion as this ion is known to form strong complexes with amines. Thus, under gastrointestinal conditions, it will not be released from the resin in appreciable quantities. Furthermore, $Fe^{3+}$ in small doses is known to be non-toxic and, indeed, has some therapeutic value.

thylenepentamine and epichlorohydrin, having repeat units of the formula:

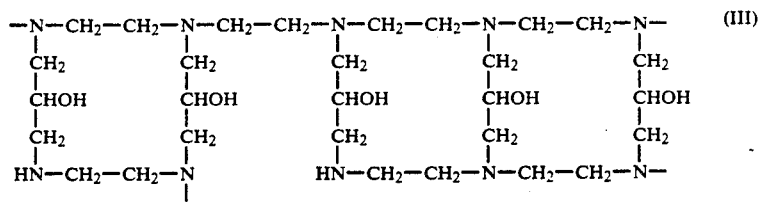

The polymer backbone to which the amino groups of the polyamine resins of formulas (Ia), (Ib) and (II) are chemically bonded must be cross-linked to prevent the sorbent from diffusing from the digestive tract, as well as non-digestible to prevent the sorbent from being broken down and absorbed into the body. A preferred hydrophilic polymer resin for use as backbone in the polyamine resins of formula (Ia) or (Ib) is a porous, cross-linked poly(methyl acrylate) resin; such a resin is advantageously prepared by polymerizing methyl acrylate in the presence of two cross-linking agents used in a ratio of 1:1. The porosity of the resin permits diffusion of the bile salts which are to be sequestered, thereby improving adsorption capacity. A cross-linked poly(glycidyl methacrylate) resin can also be used as hydrophilic backbone. A preferred hydrophobic polymer resin for use as backbone in the polyamine resins of formula (II) is a cross-linked poly(p-chloromethyl styrene) resin; such a resin is sold under the trade mark BIO-BEADS S-X1 by Bio-Rad Laboratories.

Preferred metal ion coordinated polyamine resins according to the invention are those in which the chelating metal ion is a ferric ion and the polymeric amine is either (i) a polyamine resin of formula (Ia) wherein m is 1, 2, 3 or 4, n is 2, 4 or 6 and P represents a polyacrylamide or poly(glycidyl methacrylate) backbone, (ii) a polyamine resin of formula (Ib) wherein m is 1, n, o and p are each 2 and P represents a polyacrylamide or poly(glycidyl methacrylate) backbone, or (iii) a polyamine resin of formula (II) wherein m is 0, 1 or 2, n is 2 or 6 and P' represents a poly(p-methylene styrene) backbone.

Amongst the above metal ion coordinated polyamine resins, those in which the polymeric amine is either (i) a polyamine resin of formula (Ia) wherein m is 1, 2 or 3, n is 2 and P represents a polyacrylamide backbone, (ii) a polyamine resin of formula (Ib) wherein m is 1, n, o and p are each 2 and P represents a polyacrylamide backbone, or (iii) a polyamine resin of formula (II) in which m is 0, 1 or 3, n is 2 and P' represents a poly(p-methylene styrene) backbone, are particularly preferred.

It is also possible according to the invention to coordinate a non-toxic, pharmaceutically acceptable chelating metal ion such as a ferric ion with cross-linked copolymers of a polyethylenepolyamine containing from 2 to 6 ethylene units and epichlorohydrin. The preparation of such copolymers is described in U.S. Pat. No. 3,692,895, the teaching of which is incorporated herein by reference. A cross-linked copolymer of tetraethylenepentamine and epichlorohydrin, having repeat units of the formula: and sold under the trade mark COLESTID, is particularly preferred.

The metal ion coordinated polyamine resins according to the invention not only exhibit high sorption capacity but also high water-swellability, which render them suitable for clinical application.

Further features and advantages of the invention will become more readily apparent from the following non-limiting examples and the accompanying drawings, in which:

FIGS. 1 to 4 show the sorption isotherms of compounds according to the invention for sodium glycocholate in aqueous 0.050 M NaCl solution, pH=7.0, compared with the sorption isotherms of cholestyramine (FIG. 2) and COLESTID (FIG. 4), used as reference sorbents; and FIG. 5 shows the sorption isotherms of other compounds according to the invention for sodium glycocholate in 0.0025 M, pH=7.1, Tris buffer.

1. Synthesis of Polyamine Resins with Hydrophilic Backbone a) Poly(methyl acrylate) based resins Using benzoyl peroxide as initiator, butyl ether as pore forming agent and poly(vinyl alcohol) as surfactant, beads of a porous, cross-linked poly(methyl acrylate) (PMA) resin were synthesized by suspension polymerization of methyl acrylate, divinyl benzene and triallyl-1,3,5-triazine-2,4,6,(1H,3H,5H)-trione. Functionalization of the PMA resin with a di-, tri- or tetraamine was carried out in a 200 ml 3-necked flask equipped with a mechanical stirrer, a condenser, a thermometer, $CaCO_3$ drying tube was immersed in an oil bath. 5 grams of PMA and 100 ml of an alkylamine were added into the flask and stirred for one hour at room temperature. The temperature was then increased to 50° C. and was maintained for 3 hours. Thereafter it was increased to 120° C., and maintained at this temperature for 4 days. The amine-containing resin thus obtained was washed repeatedly with methanol, and then with distilled water. It was finally dried under vacuum.

b) Poly(glycidyl methacrylate) based resins

Using 2,2'-azobis(2-methylpropionitrile) as initiator and polyvinylpyrrolidone as stabilizer, beads of a cross-linked poly(glycidyl methacrylate) resin were synthesized by suspension polymerization of glycidyl methacrylate and ethylene dimethacrylate. The content of ethylene dimethacrylate in the resin was about 5 weight %. Functionalization of the resin thus obtained was carried out in a dioxane solution with a large excess (i.e. ≧10 times, on a molar basis) of di-, tri- or tetraamine at 60°–80° C. for 8–12 hours.

2. Synthesis of Polyamine Resins with Hydrophobic Backbone 7.7 grams of a cross-linked poly(p-chloromethyl styrene) resin sold under the trade mark BIO-BEADS S-X1 by Bio-Rad Laboratories and 10 ml of N,N-dimethylformamide were mixed in a 3-necked flask equipped with a mechanical stirrer, a condenser and a stopper. The resin was allowed to swell for 20 minutes before 72 ml of an alkylamine were added. Then the reaction was allowed to proceed for three successive periods of 2, 21 and 24 hours at room temperature, 60° C. and 71° C., respectively. The amine-containing resin thus obtained was purified by washing with ethanol in a Soxhlet extractor for 24 hours, then packed into a column and washed with distilled water for 24 hours. It was finally dried under vacuum for 3 days.

3. Metal Ion Coordination of Polyamine Resins

The free amine-containing resins prepared as described above were coordinated or complexed with $FeCl_3$. This was done according to two methods.

According to the first method, before the complexation was started, the resin was preswollen with distilled water in one flask and the metallic salt was dissolved in water and filtered in another flask. The reaction was started by simply mixing the contents of the two flasks and the resulting mixture was then shaken for about 5 hours at room temperature. The product was washed repeatedly with distilled water until no $Cl^-$ came out from the resin.

According to the second method, the resin was swelled with methanol and reacted with an anhydrous $FeCl_3$ methanolic solution at 60° C. for 6-8 hours. The system was then aerated with dry HCl gas for 1 hour and filtered, washed with methanol and dried in vacuum.

4. Characterization of the Sorbents

The products were characterized both qualitatively by infrared spectroscopy and quantitatively by acid-base back titration. FT-IR measurements confirmed that the various amines had been chemically attached to the polymer backbone. From acid-base back titration, it was found that the amine functionalities of the resins were in the range of 5-9 mmol/g (dry). The metal ion contents of the adsorbents were determined to range from 2 to 10 weight %.

5. Sorption Studies a) Using bile acids in NaCl solution

A bile salt solution with a concentration of about 50 mg/dl was prepared with 0.05M NaCl aqueous solution, pH=7.0. Into bottles of different sizes (2-50 ml), about 5-15 mg of the resin to be tested was weighed. Then different volumes of bile salt solution (1-30 ml) were added into the bottles. By changing the volumes of the bile salt solution added, a whole range of bile salt equilibrium concentrations was easily reached. They were shaken at room temperature (15°-25° C.) for more than 2 hours. Then they were filtered and the clear solutions were analyzed by High Performance Liquid Chromatography (HPLC).

b) Using bile acids in Tris buffer

Tris(hydroxymethyl)-aminomethane (Aldrich) and 1.000 N standard HCl solution were used to prepare a buffered solution with ionic strength 0.0025 M and pH=7.1. With this buffer, bile salt solution with concentration about 50 mg/dl was prepared and was used directly. Into bottles of different sizes (2-100 ml), about 5-15 mg of the resin to be tested was weighed. Then different volumes of bile salt solution (1-50 ml) were added into the bottles. By changing the volumes of the bile salt solution added, a whole range of bile salt equilibrium concentrations was easily reached. Alternatively, fixed volumes of solutions initially having different acid concentrations were also used. They were shaken at room temperature (15°-25°) for more than 2 hours. Then they were filtered and the clear solutions were analyzed by HPLC.

EXAMPLE 1

A metal ion coordinated polyamine resin was prepared as described above by grafting ethylenediamine onto the cross-linked poly(methyl acrylate) resin and then reacting the polyamine resin with a dilute aqueous $FeCl_3$ solution. This material, designated "$Fe^{3+}$-resin 1", was stirred with a $Na^+$-glycocholate solution in 0.05 NaCl solution at an initial bile salt concentration of 40-60 mg/dl and at room temperature, for more than 2 hours. The amount of $Na^+$-glycocholate sorbed was measured by HPLC as described above. The sorption isotherm is shown in FIG. 1. At an equilibrium concentration of 20 mg/dl, this resin sorbed 0.050 gram of $Na^+$-glycocholate per gram of resin.

EXAMPLE 2

Example 1 was repeated except that 1,4-diaminobutane, instead of ethylenediamine, was grafted onto the poly(methyl acrylate) resin. The product obtained, designated "$FE^{3+}$-resin 2", sorbed 0.020 gram of $Na^+$-glycocholate cholate per gram of resin at an equilibrium concentration of 20 mg/dl. The sorption isotherm is shown in FIG. 1.

EXAMPLE 3

Example 1 was repeated except that 1,6-hexanediamine, instead of ethylenediamine, was grafted onto the poly(methyl acrylate) resin. The product obtained, designated "$Fe^{3+}$-resin 3", sorbed 0.030 gram of $Na^+$-glycocholate per gram of resin at an equilibrium concentration of 20 mg/dl. The sorption isotherm is shown in FIG. 1.

EXAMPLE 4

Example 1 was repeated except that diethylenetetraamine, instead of ethylenediamine, was grafted onto the poly(methyl acrylate) resin. The product obtained, designated "$Fe^{3+}$-resin 4", sorbed 0.080 gram of $Na^+$-glycocholate per gram of resin at an equilibrium concentration of 20 mg/dl. The sorption isotherm is shown in FIG. 1.

EXAMPLE 5

Figure 2:
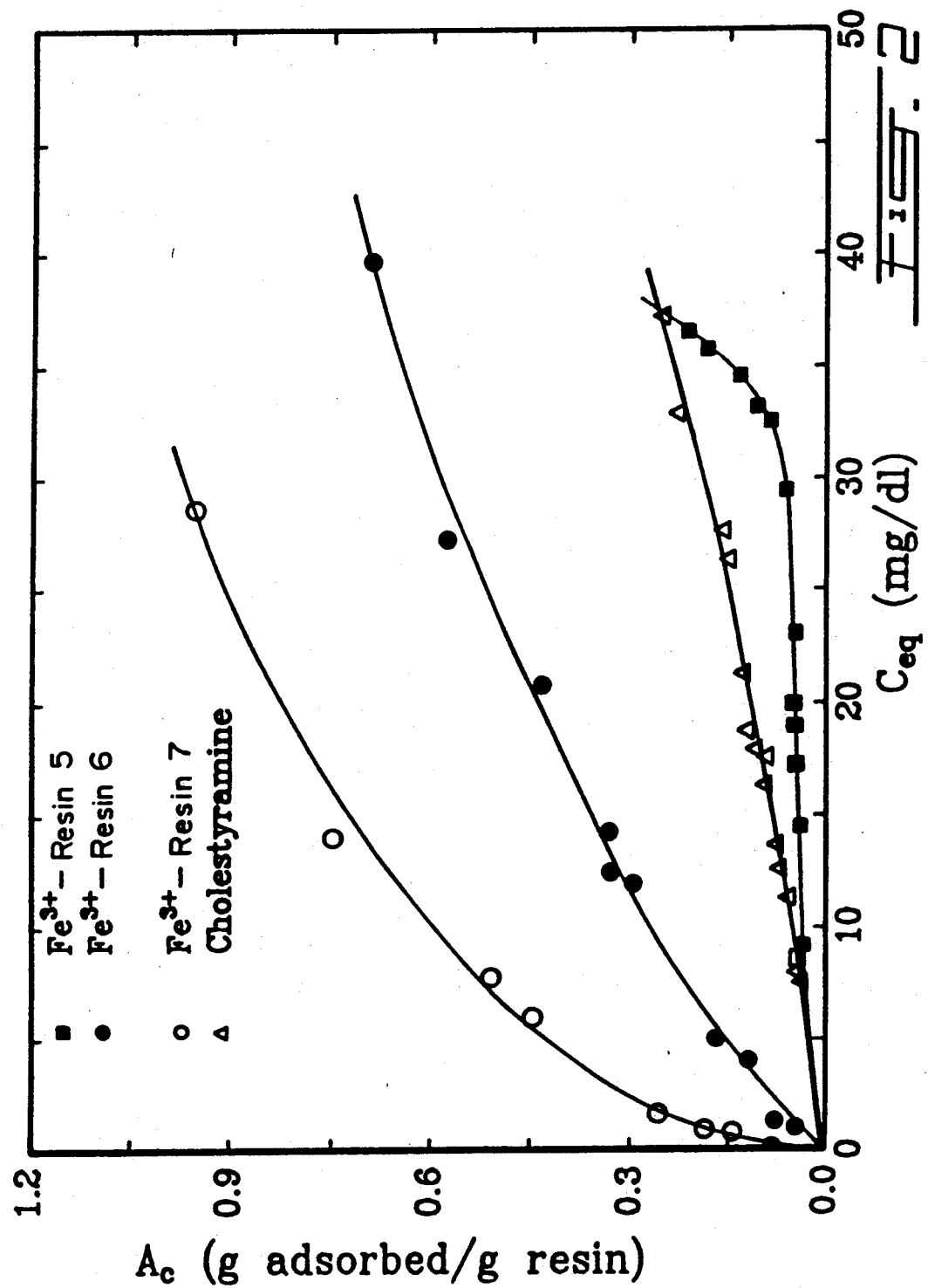

Example 1 was repeated except that triethylenetetraamine, instead of ethylenediamine, was grafted onto the poly(methyl acrylate) resin. The product obtained, designated "$Fe^{3+}$-resin 5", sorbed 0.050 gram of $Na^+$-glycocholate per gram of resin at an equilibrium concentration of mg/dl. The sorption isotherm is shown in FIG. 2.

EXAMPLE 6

A metal ion coordinated polyamine resin was prepared as described above by reacting a cross-linked poly(methylamine styrene) resin sold under the trade mark D-380 (available from Nankai Chemical Co., Nankai, Tianjin, China) with a dilute aqueous $FeCl_3$ solution. Before complexation, the resin was purified by washing with methanol and distilled water. The product obtained, designated "$Fe^{3+}$-resin 6", was tested for the sorption of $Na^+$-glycocholate in the manner described in Example 1. The sorption isotherm is shown in FIG. 2. At an equilibrium concentration of 20 mg/dl, this resin sorbed 0.44 gram of $Na^+$-glycocholate per gram of resin.

EXAMPLE 7

A metal ion coordinated polyamine resin was prepared as described above by grafting triethylenetetraamine onto the cross-linked poly(chloromethyl styrene) resin (BIO-BEADS S-X1) and then reacting the polyamine resin with a dilute aqueous $FeCl_3$ solution. The product obtained, designated "$Fe^{3+}$-resin 7", was tested for the sorption of $Na^+$-glycocholate in the manner described in Example 1. The sorption isotherm is shown in FIG. 2. At an equilibrium concentration of 20 mg/dl, this resin sorbed 0.83 gram of $Na^{30}$-glycocholate per gram of resin.

EXAMPLE 8

Example 7 was repeated except that ethylenediamine, instead of triethylenetetraamine was grafted onto the poly(chloromethyl styrene) resin. The product obtained, designated "$Fe^{3+}$-resin 8", sorbed 0.70 gram of $Na^+$-glycocholate per gram of resin at an equilibrium concentration of 20 mg/dl. The sorption isotherm is shown in FIG. 2.

EXAMPLE 9

Figure 3:
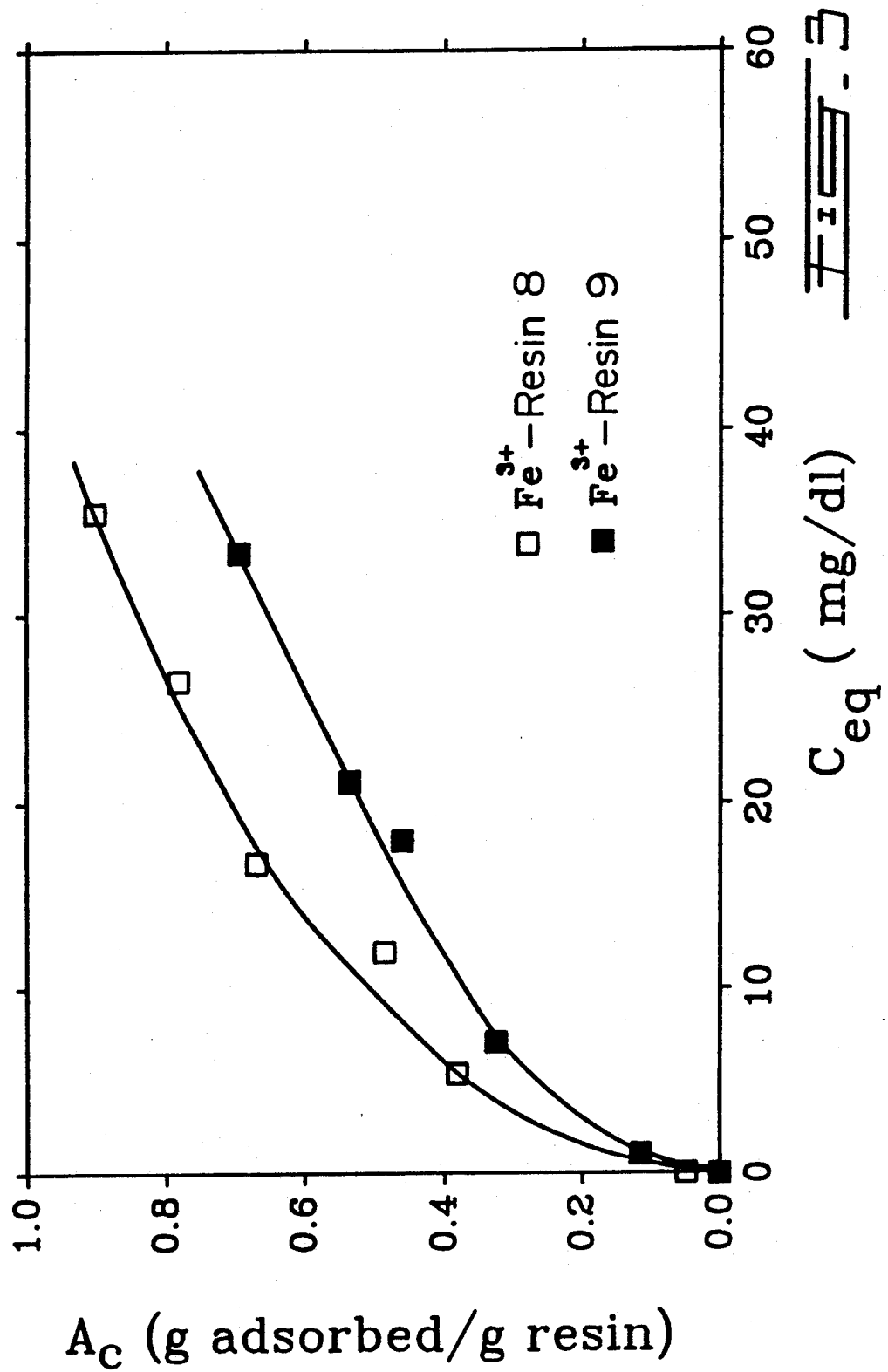

Example 7 was repeated except that 1,6-hexanediamine, instead of triethylenetetraamine was grafted onto the poly(chloromethyl styrene) resin. The product obtained, designated "$Fe^{3+}$-resin 9", sorbed 0.48 gram of $Na^+$-glycocholate per gram of resin at an equilibrium concentration of 20 mg/dl. The sorption isotherm is shown in FIG. 3.

EXAMPLE 10

Figure 4:
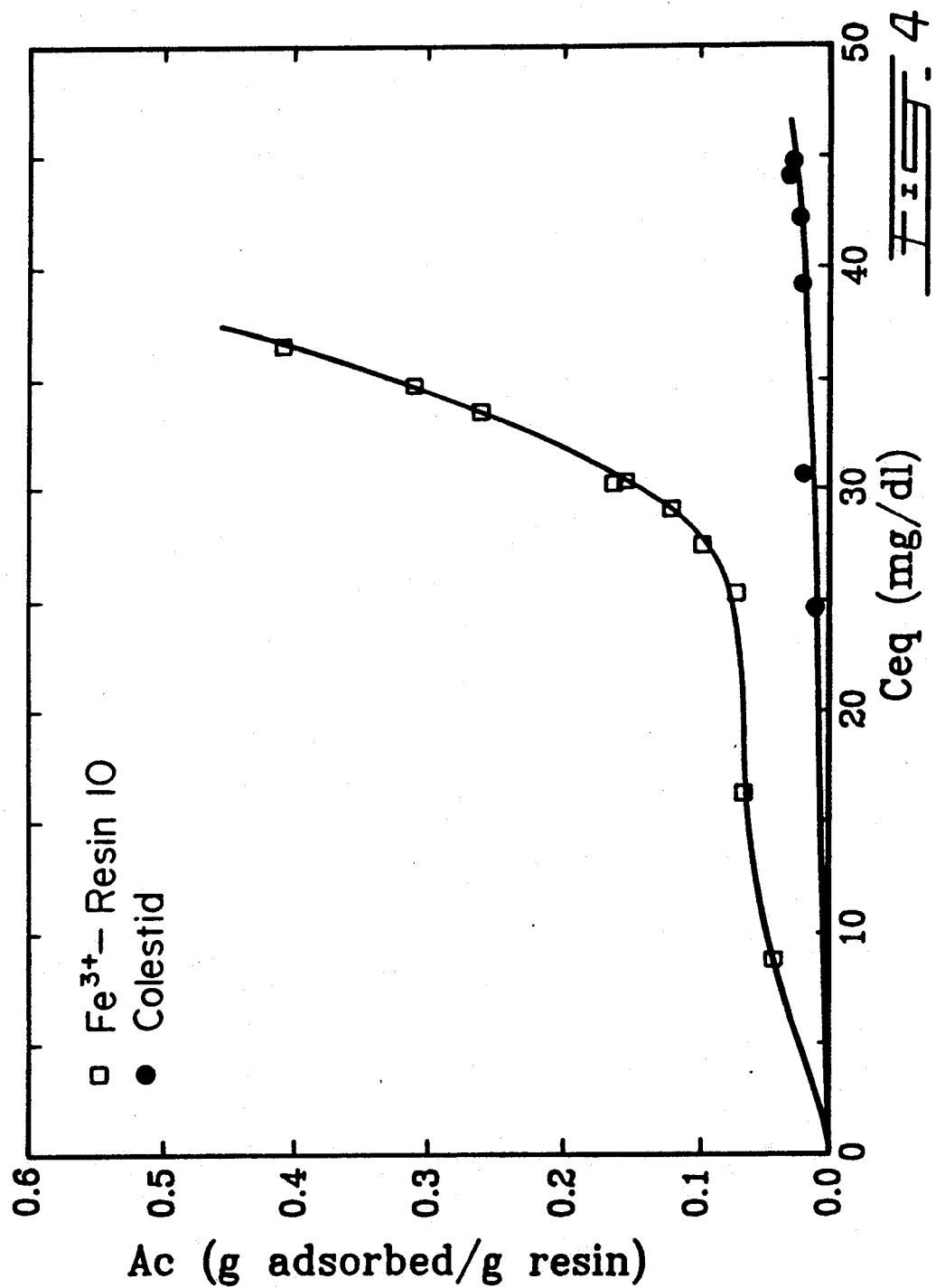

A metal ion coordinated polyamine resin was prepared as described above by reacting a cross-linked copolymer of tetraethylenepentamine and epichlorohydrin sold under the trade mark COLESTID with a dilute aqueous $FeCl_3$ solution. Before complexation, the copolymer was treated with a dilute NaOH solution to convert all the protonated amine groups to free amine groups; excess NaOH was washed away with distilled water. The product obtained, designated "$Fe^{3+}$-resin 10", was tested for the sorption of $Na^+$-glycocholate in the manner described in Example 1. The sorption isotherm is shown in FIG. 4. At an equilibrium concentration of 20 mg/dl, this resin sorbed 0.060 gram of $Na^{30}$-glycocholate per gram of resin.

EXAMPLE 11

A metal ion coordinated polyamine resin was prepared as described above by grafting tetraethylenepentamine onto the cross-linked poly(methyl acrylate) resin and then reacting the polyamine resin with an anhydrous $FeCl_3$ methanolic solution. This material, designated "$Fe^{3+}$-resin 11", was stirred with a $Na^{30}$-glycocholate solution in Tris buffer at an initial bile salt concentration of 30–50 mg/dl for more than 8 hours. The amount $Na^{30}$-glycocholate sorbed was measured by HPLC as described above. The sorption isotherm is shown in FIG. 5. At an equilibrium concentration of 20 mg/dl, this resin sorbed 0.90 gram of $Na^+$-glycocholate per gram of resin.

EXAMPLE 12

Example 11 was repeated except that tris(2-aminoethyl)amine, instead of tetraethylenepentamine was grafted onto the poly(methyl acrylate)resin. The product obtained, designated "$Fe^{3+}$-resin 12", sorbed 0.62 gram of $Na^{30}$-glycocholate per gram of resin at an equilibrium concentration of 20 mg/dl. The sorption isotherm is shown in FIG. 5.

EXAMPLE 13

A metal ion coordinated polyamine resin was prepared as described above by grafting triethylenetetraamine onto the cross-linked poly(glycidyl methacrylate) resin and then reacting the polyamine resin with an anhydrous $FeCl_3$ methanolic solution. The product obtained, designated "$Fe^{3+}$-resin 13", was tested for the sorption of $Na^{30}$-glycocholate in the manner described in Example 11. The sorption isotherm is shown in FIG. 5. At an equilibrium concentration of 20 mg/dl, this resin sorbed 0.080 gram of $Na^+$-glycocholate per gram of resin.

EXAMPLE 14

Example 13 was repeated except that tris(2-aminoethyl)amine, instead of triethylenetetraamine was grafted onto the poly(glycidyl methacrylate) resin. The product obtained, designated "$Fe^{3+}$-resin 14", sorbed 0.16 gram of $Na^+$-glycocholate per gram of resin at an equilibrium concentration of 20 mg/dl. The sorption isotherm is shown in FIG. 5.

The sorption capacities of the metal ion coordinated polyamine resins prepared in Examples 1 through 14 are summarized in the following Table:

TABLE

| Ex. No. | Product Designation | Structure of Polymeric Amine | Sorption Capacity (*) |
|---|---|---|---|
| 1 | $Fe^{3+}$-resin 1 | $P_1-(CH_2)_2NH_2$ | 0.050 |
| 2 | $Fe^{3+}$-resin 2 | $P_1-(CH_2)_4NH_2$ | 0.020 |
| 3 | $Fe^{3+}$-resin 3 | $P_1-(CH_2)_6NH_2$ | 0.030 |
| 4 | $Fe^{3+}$-resin 4 | $P_1-[(CH_2)_2NH]_2H$ | 0.080 |
| 5 | $Fe^{3+}$-resin 5 | $P_1-[(CH_2)_2NH]_3H$ | 0.050 |
| 6 | $Fe^{3+}$-resin 6 | $P_2-NH_2$ | 0.44 |
| 7 | $Fe^{3+}$-resin 7 | $P_2-[NH(CH_2)_2]_3NH_2$ | 0.83 |
| 8 | $Fe^{3+}$-resin 8 | $P_2-NH(CH_2)_2NH_2$ | 0.70 |
| 9 | $Fe^{3+}$-resin 9 | $P_2-NH(CH_2)_6NH_2$ | 0.48 |
| 10 | $Fe^{3+}$-resin 10 | See formula (III) on page 6 | 0.060 |
| 11 | $Fe^{3+}$-resin 11 | $P_1-[(CH_2)_2NH]_4H$ | 0.90 |
| 12 | $Fe^{3+}$-resin 12 | $P_1-(CH_2)_2-N\begin{array}{l}(CH_2)_2NH_2\\(CH_2)_2NH_2\end{array}$ | 0.62 |
| 13 | $Fe^{3+}$-resin 13 | $P_3-[(CH_2)_2NH]_3H$ | 0.080 |

TABLE-continued

| Ex. No. | Product Designation | Structure of Polymeric Amine | Sorption Capacity (*) |
|---|---|---|---|
| 14 | $Fe^{3+}$-resin 14 | $P_3-(CH_2)-N\begin{matrix}(CH_2)_2NH_2\\(CH_2)_2NH_2\end{matrix}$ | 0.16 |

$P_1$ = polyacrylamide backbone
$P_2$ = poly(p-methylene styrene) backbone
$P_3$ = poly(glycidyl methacrylate) backbone
(*) gram of sodium glycocholate sorbed per gram of resin (at an equilibrium concentration of 20 mg/dl).

As it is apparent from the above Table, the metal ion coordinated polyamine resins of the invention are effective in binding bile acids, to an extent that is strongly dependent on the structure of the amine functional group. As shown in FIGS. 1, 2 and 5, the resins with the hydrophilic backbone ($P_1$ or $P_3$) exhibit increased bile acid sorption with increased hydrophobicity of the amine functional group. This is particularly evident at high bile acid concentrations (>30 mg/dl) when they are much more effective than cholestyramine, under similar conditions. Similar behaviour is demonstrated by the $Fe^{3+}$-containing COLESTID, i.e. $Fe^{3+}$-resin 10 (FIG. 4). On the other hand, as it is apparent form FIGS. 2, 3 and 5, the resins with the hydrophobic backbone ($P_2$) are much more effective than cholestyramine at all bile acid concentrations.

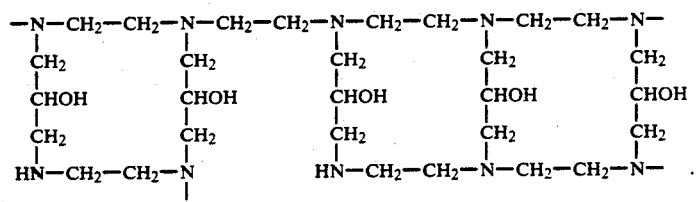

We claim:

1. A ferric ion coordinated polyamine resin in which a ferric ion is coordinated with a cross-linked and non-digestible polymeric amine selected from the group consisting of:

a) polyamine resins with a hydrophilic backbone, of the formula:

$$P-[(CH_2)_nNH]_mH \text{ or } P-(CH_2)_n-N\begin{matrix}[(CH_2)_oNH]_mH\\{}\\{[(CH_2)_pNH]_mH}\end{matrix}$$

(Ia)                                          (Ib)

wherein P represents a hydrophilic, cross-linked and non-digestible homopolymer backbone, m is an integer varying from 1 to 10 inclusive, and n, o and p are, independently, integers varying from 2 to 12 inclusive;

b) polyamine resins with a hydrophobic backbone, of the formula:

$$P'-[NH(CH_2)_n]_mNH_2 \quad (II)$$

wherein P' represents a hydrophobic, cross-linked and non-digestible homopolymer backbone, m is an integer varying form 0 to 6 inclusive and n is an integer varying from 2 to 12 inclusive; and c) cross-linked copolymers of a polyethylenepolyamine containing from 2 to 6 ethylene units and epichlorohydrin;

said ferric ion being present in an amount ranging from 2 to 10 weight % of said ferric ion coordinated polyamine resin.

2. A ferric ion coordinated polyamine resin as claimed in cl aim 1, wherein the polymeric amine is a polyamine resin of formula (Ia) in which m is 1, 2, 3 or 4, n is 2, 4 or 6 and P has the aforesaid meaning.

3. A ferric ion coordinated polyamine resin as claimed in claim 2, wherein P represents a polyacrylamide or poly(glycidyl methacrylate) backbone.

4. A ferric ion coordinated polyamine resin as claimed in claim 1, wherein the polymeric amine is a polyamine resin of formula (Ia) in which m is 1, 2 or 3, n is 2 and P represents a polyacrylamide backbone.

5. A ferric ion coordinated polyamine resin as claimed in claim 1, wherein the polymeric amine is a polyamine resin of formula (Ib) in which m is 1, n, o and p are each 2 and P has the aforesaid meaning.

6. A ferric ion coordinated polyamine resin as claimed in claim 5, wherein P represents a polyacrylamide or poly(glycidyl methacrylate) backbone.

7. A ferric ion coordinated polyamine resin as claimed in claim 1, wherein the polymeric amine is a polyamine resin of formula (Ib) in which m is 1, n, o and p are each 2 and P represents a polyacrylamide backbone.

8. A ferric ion coordinated polyamine resin as claimed in claim 1, wherein the polymeric amine is a polyamine resin of formula (II) in which m is 0, 1 or 3, n is 2 or 6 and P' has the aforesaid meaning.

9. A ferric ion coordinated polyamine resin as claimed in claim 8, wherein P' represents a poly(p-methylene styrene) backbone.

10. A ferric ion coordinated polyamine resin as claimed in claim 1, wherein the polymeric amine is a polyamine resin of formula (II) in which m is 1 or 3, n is 2 and P' represents a poly(p-methylene styrene) backbone.

11. A ferric ion coordinated polyamine resin as claimed in claim 1, wherein the polymeric amine is a polyamine resin of formula (II) in which m is 0 and P' represents a poly(p-methylene styrene) backbone.

12. A ferric ion coordinated polyamine resin as claimed in claim 1, wherein the polymeric amine is a cross-linked copolymer of tetraethylenepentamine and epichlorohydrin, having repeat units of the formula:

$$\begin{matrix}-N-CH_2-CH_2-N-CH_2-CH_2-N-CH_2-CH_2-N-CH_2-CH_2-N-\\|\quad\quad\quad\quad|\quad\quad\quad\quad|\quad\quad\quad\quad|\quad\quad\quad\quad|\\CH_2\quad\quad CH_2\quad\quad CH_2\quad\quad CH_2\quad\quad CH_2\\|\quad\quad\quad\quad|\quad\quad\quad\quad|\quad\quad\quad\quad|\quad\quad\quad\quad|\\CHOH\quad CHOH\quad CHOH\quad CHOH\quad CHOH\\|\quad\quad\quad\quad|\quad\quad\quad\quad|\quad\quad\quad\quad|\quad\quad\quad\quad|\\CH_2\quad\quad CH_2\quad\quad CH_2\quad\quad CH_2\quad\quad CH_2\\|\quad\quad\quad\quad|\quad\quad\quad\quad\quad\quad\quad\quad|\quad\quad\quad\quad|\\HN-CH_2-CH_2-N\quad\quad\quad HN-CH_2-CH_2-N-CH_2-CH_2-N-\end{matrix}$$

13. A pharmaceutical composition for the treatment of hypercholesterolemia, which comprises as active ingredient a ferric ion coordinated polyamine resin in which a ferric ion is coordinated with a cross-linked and non-digestible polymeric amine selected from the group consisting of:

a) polyamine resins with a hydrophilic backbone, of the formula:

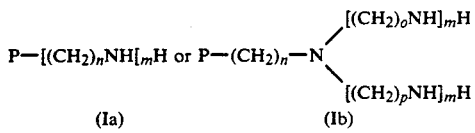

(Ia) (Ib)

wherein P represents a hydrophilic, cross-linked and non-digestible homopolymer backbone, m is an integer varying from 1 to 10 inclusive, and n, o and p are, independently, integers varying from 2 to 12 inclusive;

b) polyamine resins with a hydrophobic backbone, of the formula:

P'-[NH(CH$_2$)$_n$]$_m$NH$_2$        (II)

wherein P' represents a hydrophobic, cross-linked and non-digestible homopolymer backbone, m is an integer varying from 0 to 6 inclusive and n is an integer varying from 2 to 12 inclusive; and c) cross-linked copolymers of a polyethylenepolyamine containing from 2 to 6 ethylene units and epichlorohydrin;

together with a pharmaceutically acceptable carrier therefor, said ferric ion being present in said ferric ion coordinated polyamine resin in an amount ranging from 2 to 10 weight %.

14. A pharmaceutical composition as claimed in claim 13, wherein the active ingredient is a ferric ion coordinated polyamine resin in which said ferric ion is coordinated with a polyamine resin of formula (Ia) in which m is 1, 2 or 3, n is 2 and P represents a polyacrylamide backbone.

15. A pharmaceutical composition as claimed in claim 13, wherein the active ingredient is a ferric ion coordinated polyamine resin in which a ferric ion is coordinated with a polyamine resin of formula (Ib) in which m is 1, n, o and p are each 2 and P represents a polyacrylamide backbone.

16. A pharmaceutical composition as claimed in claim 13, wherein the active ingredient is a ferric ion coordinated polyamine resin in which said ferric ion is coordinated with a polyamine resin of formula (II) in which m is 0, 1 or 3, n is 2 or 6 and P' represents a poly(p-methylene styrene) backbone.

17. A pharmaceutical composition as claimed in cl aim 13, wherein the active ingredient is a ferric ion coordinated polyamine resin in which said ferric ion is coordinated with a polyamine resin of formula (II) in which m is 1 or 3, n is 2 and P' represents a poly(p-methylene styrene) backbone.

18. A pharmaceutical composition as claimed in claim 13, wherein the active ingredient is a ferric ion coordinated polyamine resin in which said ferric ion is coordinated with a polyamine resin of formula (II) in which m is 0 and P' represents a poly(p-methylene styrene) backbone.

19. A pharmaceutical composition as claimed in claim 13, wherein the active ingredient is a ferric ion coordinated polyamine resin in which said ferric ion is coordinated with a cross-linked copolymer of tetraethylenepentamine and epichlorohydrin, having repeat units of the formula:

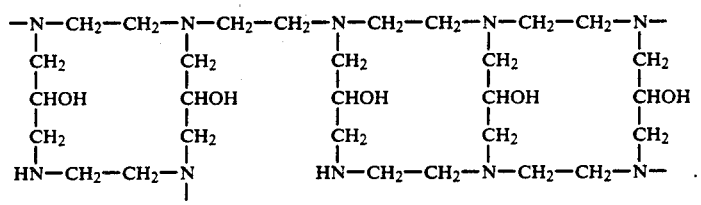

20. A method of treating hypercholesterolemia in an affected human, which comprises administering to said human an effective amount of a bile salt sorbent consisting of a ferric ion coordinated polyamine resin in which a ferric ion is coordinated with a cross-linked and non-digestible polymeric amine selected from the group consisting of:

a) polyamine resins with a hydrophilic backbone, of the formula:

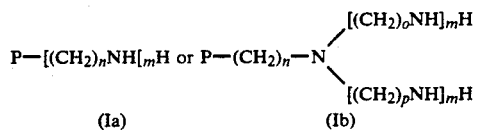

(Ia) (Ib)

wherein P represents a hydrophilic, cross-linked and non-digestible homopolymer backbone, m is an integer varying from 1 to 10 inclusive, and n, o and p are, independently, integers varying from 2 to 12 inclusive;

b) polyamine resins with a hydrophobic backbone, of the formula:

P' [NH(CH$_2$)$_n$]$_m$NH$_2$        (II)

wherein P' represents a hydrophobic, cross-linked and non-digestible homopolymer backbone, m is an integer varying from 0 to 6 inclusive and n is an integer varying from 2 to 12 inclusive; and c) cross-linked copolymers of a polyethylenepolyamine containing from 2 to 6 ethylene units and epichlorohydrin said ferric ion being present in a range of 2–10% of said polymeric amine.

21. A method as claimed in claim 20, wherein the bile salt sorbent is a ferric ion coordinated polyamine resin in which said ferric ion is coordinated with a polyamine resin of formula (Ia) in which m is 1, 2 or 3, n is 2 and P represents a polyacrylamide backbone.

22. A method as claimed in claim 20, wherein the bile salt sorbent is a ferric ion coordinated polyamine resin in which said ferric ion is coordinated with a polyamine resin of formula (Ib) in which m is 1, n, o and p are each 2 and P represents a polyacrylamide backbone.

23. A method as claimed in claim 20, wherein the bile salt sorbent is a ferric ion coordinated polyamine resin in which the polymeric amine is a polyamine resin of formula (II) in which m is 0, 1 or 3, n is 2 or 6 and P' has the aforesaid meaning.

24. A method as claimed in claim 20, wherein the bile salt sorbent is a ferric ion coordinated polyamine resin in which said ferric ion is coordinated with a polyamine resin of formula (II) in which m is 0, 1 or 3, n is 2 or 6 and P' represents a poly(p-methylene styrene) backbone.

25. A method as claimed in claim 20, wherein the bile salt sorbent is a ferric ion coordinated polyamine resin in which said ferric ion is coordinated with a polyamine resin of formula (II) in which m is 1 or 3, n is 2 and P' represents a poly(p-methylene styrene) backbone.

26. A method as claimed in claim 20, wherein the bile salt sorbent is a ferric ion coordinated polyamine resin in which said ferric ion is coordinated with a polyamine resin of formula (II) in which m is 0 and P' represents a poly(p-methylene styrene) backbone.

27. A method as claimed in claim 20, wherein the bile salt sorbent is a ferric ion coordinated polyamine resin in which said ferric ion is coordinated with a cross-linked copolymer of tetraethylenepentamine and epichlorohydrin, having repeat units of the formula: